United States Patent [19]

Chivé Maurice et al.

[11] Patent Number: 5,176,146
[45] Date of Patent: Jan. 5, 1993

[54] METHOD FOR THE MEASUREMENT OF TEMPERATURES BY MICROWAVE RADIOMETRY, WITH AUTOMATIC CALIBRATION OF THE MEASUREMENT, AND DEVICE FOR OPERATING THIS METHOD

[75] Inventors: Chivé Maurice, Villeneuve D'Asco; Jean-Pierre Sozanski; Yves Moschetto, both of Lille Cedex; Daniel VanLoot, Villeneuve D'Asco, all of France

[73] Assignee: Institut National de la Sante et de la Recherche Medicale, Paris, France

[21] Appl. No.: 739,098

[22] Filed: Aug. 1, 1991

[51] Int. Cl.⁵ .............................................. A61B 5/00
[52] U.S. Cl. ..................................... 128/736; 374/122
[58] Field of Search ................. 128/736, 653; 374/122

[56] References Cited

U.S. PATENT DOCUMENTS

| | | |
|---|---|---|
| 3,564,420 | 2/1971 | Webb . |
| 4,557,272 | 12/1985 | Carr ..................................... 128/736 |
| 4,583,869 | 4/1986 | Chive et al. ......................... 128/736 |
| 4,627,442 | 12/1986 | Land .................................... 128/736 |
| 4,677,988 | 7/1987 | Constant et al. ..................... 128/736 |

FOREIGN PATENT DOCUMENTS 2497947 7/1981 France .

OTHER PUBLICATIONS

IEEE Transactions on Microwave Theory and Techniques, vol. MTT-16, No. 9, 9/68, pp. 629-636; HACH; "A Very Sensitive Airborne Microwave Radiometer Using Two Reference Temperatures".

*Primary Examiner*—Max Hindenburg
*Attorney, Agent, or Firm*—Larson & Taylor

[57] ABSTRACT

The device comprises a microwave detector, a short-circuit microwave, a first modulator, or microwave-switch, a circulator with three successive channels, at least two sources of internal reference temperatures, a second modulator or microwave-switch, possibly an attenuator, a synchronization command circuit acting both on the first modulator and on the second modulator to obtain at least four different successive outgoing signals, a microwave detector, advantageously a microwave amplifier, and a calculator connected to the output of synchronization command circuit, said at least four successive signals being detected to deduce therefrom the temperature at the detector level, independently of the coefficient of reflection of the detector with respect to the region of the losses and of the modulators and of the cables.

9 Claims, 6 Drawing Sheets

METHOD FOR THE MEASUREMENT OF TEMPERATURES BY MICROWAVE RADIOMETRY, WITH AUTOMATIC CALIBRATION OF THE MEASUREMENT, AND DEVICE FOR OPERATING THIS METHOD

BACKGROUND OF THE INVENTION

The invention relates to the measurement of the temperature of a particular region, especially (but not exclusively) in a human body for medical purposes, by employing hyperfrequency waves, or microwaves, in the range of 0.5 to 20 GHz.

In practice such a measurement is generally made by means of a microwave radiometer comprising:

a microwave detector (constituted in particular by an antenna or a probe) placed in contact or in immediate proximity to the region, of which it is necessary to measure the temperature and which generates a thermal noise constituted by the emission of microwaves in the aforesaid range of frequencies, said detector emitting a microwave output signal whose intensity is a function of said temperature, a thermal reference source maintained at a known temperature, possible adjustable, emitting a signal of this known temperature, and electronic detection and comparison means to deduce, from the output signal of said detector and from the output signal of said source, the temperature of said region.

Such a radiometer is described, for example, in French patent 2.497.947 and U.S. Pat. No. 4,627,442 (to which corresponds the published European patent application 0.114.094).

The most difficult problem posed by the determination of the temperature of a region by means of thermal noise microwaves emitted by this region is that of the calibration, since the signal resulting from the treatment of the microwaves emitted by said region is difficult to connect with the effective temperature of this zone, even when a reference temperature source is employed and a zero method in the comparison of the signals emitted by the region and said source, particularly on account of numerous derivatives resulting from the use of said source.

It is an object of the present invention to resolve this formidable problem of calibration and to permit thus an exact measurement by microwaves of the temperature of a predetermined region.

GENERAL DESCRIPTION OF THE INVENTION

Accordingly it is an object of the invention to provide a method for the measurement of the temperature of a region by collecting, by means of a detector, the thermal noise microwaves emitted by this region and by using a microwave short-circuit, characterised in that the thermal noise microwaves are also collected from at least two internal reference temperature sources, so that cyclic sampling over time is performed, at least the four signals resulting from the microwaves collected from this region and derived from this short-circuit, on the one hand, and from each of the two reference sources on the other hand, in order to determine a response indicating the temperature of said region, without interfering influences produced by the thermic derivatives or variations of the reflection coefficient of the detector with respect to the region;

a device for carrying out the method abovementioned comprising a microwave detector, a microwave short-circuit, a modulator or microwave switch, called below first modulator, with two connected input channels, one to the output of the detector, and the other, to the microwave short-circuit and an output connectable to one or the other of these two inputs, a circulator with three successive channels, the first being connected to the output from the first modulator, the second to the input of an electronic microwave processing unit and the third constituting a reference input, characterised in that it comprises in addition at least two reference sources of internal temperature and a second modulator or microwave switch with at least two input channels each connected to the output of one of said at least two reference sources and an output connected to said reference input of the circulator, possibly through an attenuator, and wherein said electronic unit comprises:

a synchronisation control circuit acting both on the first modulator and on the second modulator to obtain at least four different successive outgoing signals, each of said at least four signals corresponding to each one of the at least four possibilities of connection of the two modulators, the first with two input channels and the second with at least two input channels;

a microwave detector with an input connected advantageously through a microwave amplifier, to the output of the circulator and one output; and a calculator connected to the output of said detector and adapted to process, under the control of said synchronisation control circuit, said at least four detected successive signals to deduce therefrom the temperature at the level of the detector, independently of the coefficient of reflection of the detector with respect to the region and the losses of the modulators and of the cables.

Advantageously the device comprises, to perform the selection of the said at least four signals and their successive transmission to the input of the calculator:

either a high-gain low-frequency amplifier, whose input connected to the output of said microwave detector, at least four switches arranged in parallel between a common input connected to the output of said low-frequency amplifier and at least four outputs of which one, and one alone, is supplied, under the control of the synchronisation control circuit, in synchronisation with the control of the two modulators, to supply in its turn one, and one alone, among at least four averaging-integrators and two differential amplifiers of which the four inputs are connected each to the output of one of the four averaging-integrators to effect two differences, namely between the output from the first averaging-integrator and the output of the second averaging-integrator on the one hand, and between the output of the third averaging-integrator and the output of the fourth averaging-integrator, on the other hand;

or a high-gain, low-frequency amplifier, whose input is connected to the output of said microwave detector and an analog-digital converter whose input is connected to the output of said low-frequency amplifier and of which the output is connected to the input of a processing unit.

In the various embodiments of the calculator it is preferably associated with display means.

GENERAL DESCRIPTION OF THE DRAWINGS

The invention will be better understood, in any case, by means of the addition of the description which follows, as well as the accompanying drawings, which supplement and drawings are, of course, given purely by way of illustration.

Figure 1:
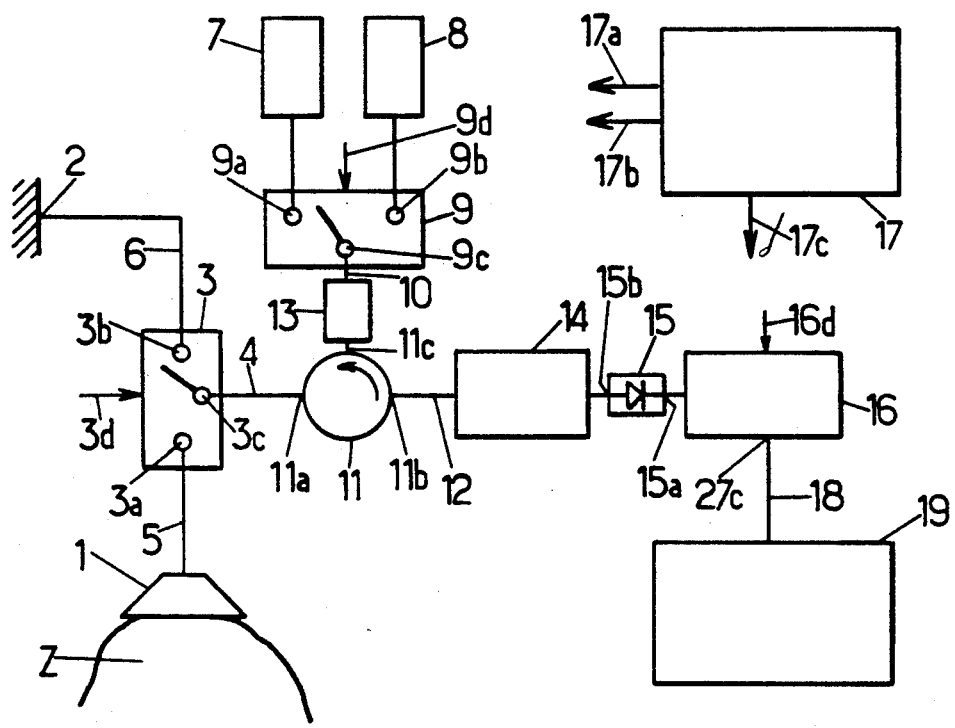
FIG. 1 shows, in the form of functional units, one embodiment of a device according to the invention with two internal temperature references.
Figure 13:
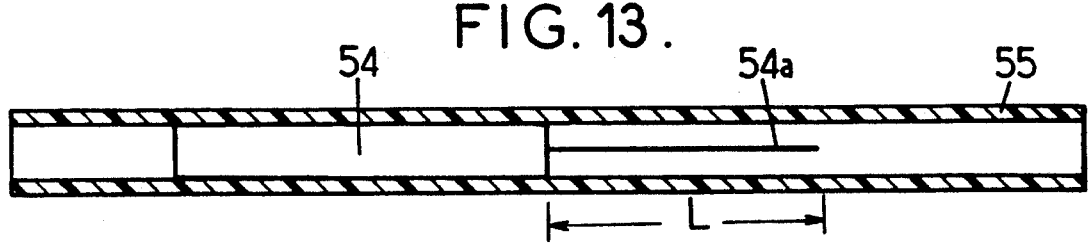

Finally, FIG. 13, shows in section, a wire antenna which can serve as a detector in a device according to FIG. 1.

DESCRIPTION OF PREFERRED EMBODIMENTS

According to the invention and more especially according to that of its types of application, as well as according to those of the embodiments of its various parts, to which it seems that preference should be given, proposing, for example, to provide a method for the measurement of temperatures by microwave radiometry, with automatic calibration of the measurement, and a device for the employment of this method, procedure is as follows or in an analogous manner.

A device according to the invention to measure the temperature of a region Z comprises (FIG. 1) first of all a detector 1, constituted by an antenna or microwave probe, which detects the microwaves emitted by this region with which it is in contact or almost in contact, the intensity of these microwaves, in a particular frequency band between 0.5 and 20 GHz, being proportional to the absolute temperature T of said region. In particular the detector may be constituted by a portion of wave guide constituted by a hollow box in the form of a rectangular parallelepiped, with an aperture facing said region, or by an antenna of the type described below with reference to FIG. 13.

The interface between the detector 1 and the region Z has a reflection coefficient r (for example slightly less than 0.2) which represents the proportion of microwave signals emitted by the region Z in the direction of the detector and reflected on the interface, hence not received by the detector. All said and done, the detector receives a microwave signal of intensity proportional to $(1-r)T$.

The device comprises in addition a microwave short-circuit 2 which effects total reflection of microwaves which are applied to it.

A first three-track microwave modulator or switch, for example of the type marketed by the GENERAL MICROWAVE company under the name MODEL F9120 or MODEL F9220, enables either the outlet from the detector 1, connected to its first input 3a, or the short-circuit 2, connected to its second input 3b, to be connected to a microwave transmission line 4, connected to the single output 3c from the modulator 3.

It should be noted that the connecting cables 5 and 6, between, on the one hand, the modulator 3 and, on the other hand, the detector 1 and the short-circuit 2 respectively, must have low losses and have the same length to have the same transmission coefficient of the microwave signals between, on the one hand, detector 1 and the short-circuit 2 respectively and on the other hand, the modulator 3.

Figure 8:
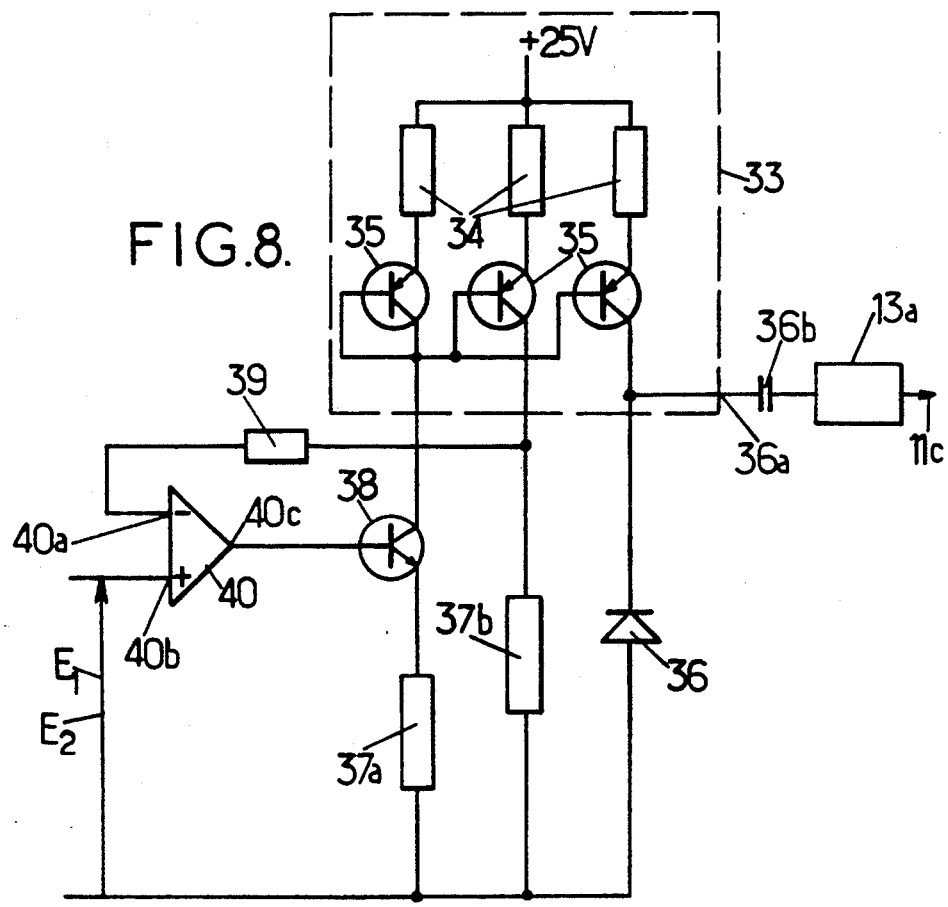
FIG. 8 shows a particular embodiment of the two reference temperature sources in a device according to FIG. 1.

In accordance with an important feature of the invention, the device comprises at least 2 microwave noise sources 7 and 8 which supply at least two reference temperatures $T_1$ and $T_2$ (absolute temperatures). These noise sources 7 and 8 may be constituted for example by two resistors of 50 ohms, of the miniature coaxial charge type marketed by the RADIALL company under the reference R404215, being maintained at the reference temperatures $T_1$ and $T_2$ which are adjusted, or constructed as illustrated in FIG. 8, which will be described below. Reference will be made in the following to two noise sources, or more generally two noise levels (case of the embodiment of FIG. 8 described below) only, corresponding to two reference temperatures.

A second microwave modulator or switch 9, with two channels, in the case of two microwave noise sources, enables either the outlet of the noise source 7, connected to its input 9a, or the outlet of the nosie source 8, connected to its input 9b, to be connected selectively to the microwave transmission line 10, connected to its output 9c.

A microwave circulator 11, with a wide band width of at least 1 GHz around the central frequency of the device (for example 1, 2 GHz, 3 GHz, 9 GHz) and with three channels, is provided between the aforementioned transmission lines 4 and 10 and output line 12, the three successive tracks 11a, 11b, 11c of the circulator 11 thus being connected:

first channel 11a, tot he line 4 (output from the first modulator 3), second channel 11b, to the output line 12, and third channel 11c, to the line 10, possibly through a microwave attenuator 13 when the noise levels on the line 10 are too high.

The output of line 12 of the portion of the device according to the invention which has just been described until now connects the second channel 11b of the circulator 11 to a wide band width microwave amplifier 14, which may for example be constituted by two amplifiers Ga As FET of 35 db, of the type marketed by the company AVANTEK under the name AMPLIFIER SA 852530, mounted in cascade to obtain a gain of 70 db, a band pass centered at 3 GHz (for example) and a noise factor of 3 db maximum.

The output from this amplifier 14 is connected to the input 15b of a microwave detector 15, for example of the type marketed by the company HEWLETT PACKARD, with the reference 8473B, having a band width of 0.01 to 18 GHz.

The unit 16 is constituted by two detectors by sampling; its input is connected to the output 15a of the detector 15.

The first detector of the unit 16 carries out the separation of the signals and the integration on the phases 1 and 2 indicated below, whilst the second detector of the unit 16 performs the same operations on the signals of the phases 3 and 4, as specified below.

Each of the two circuits effects:
switching the four signals emerging from the four phases 1,2,3,4, computing
the average of these four separate signals,
the subtraction two by two of the separated and averaged signals, and
sending the two resulting signals of the two aforesaid subtractions on to the output 27c of the unit 16.

Figure 2:
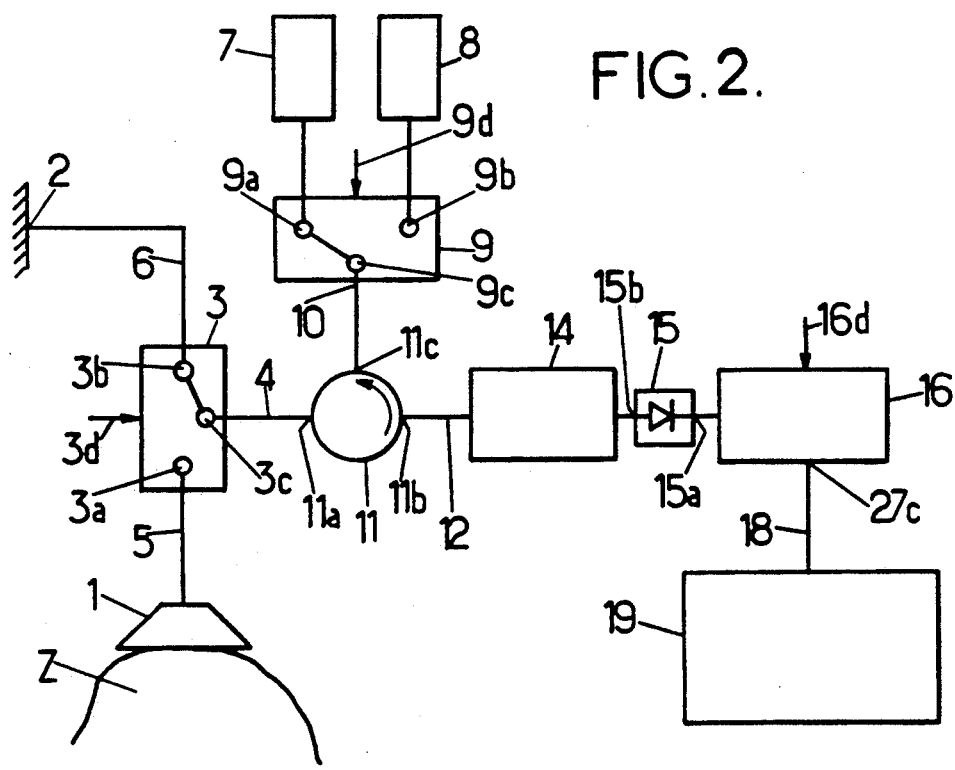
FIGS. 2 to 5 illustrate the four successive phases of a cycle of operation of the device of FIG. 1.
Figure 3:
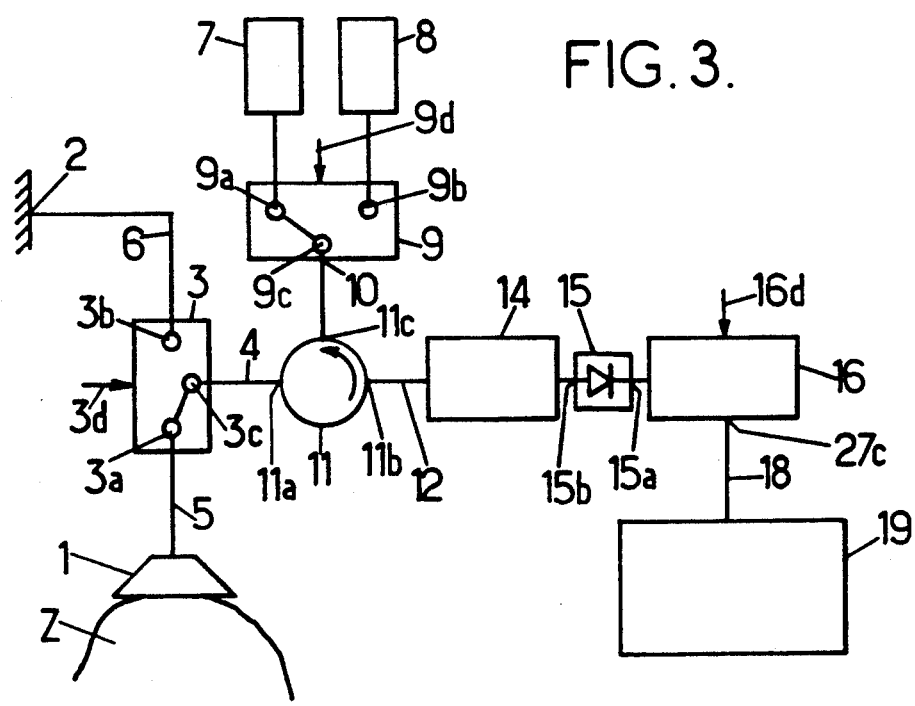
Figure 4:
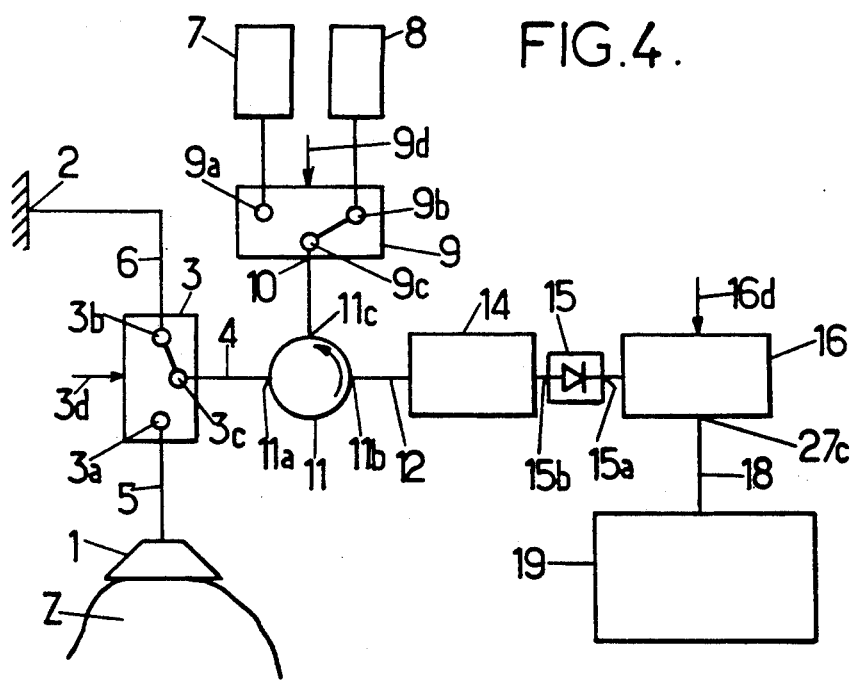
Figure 5:
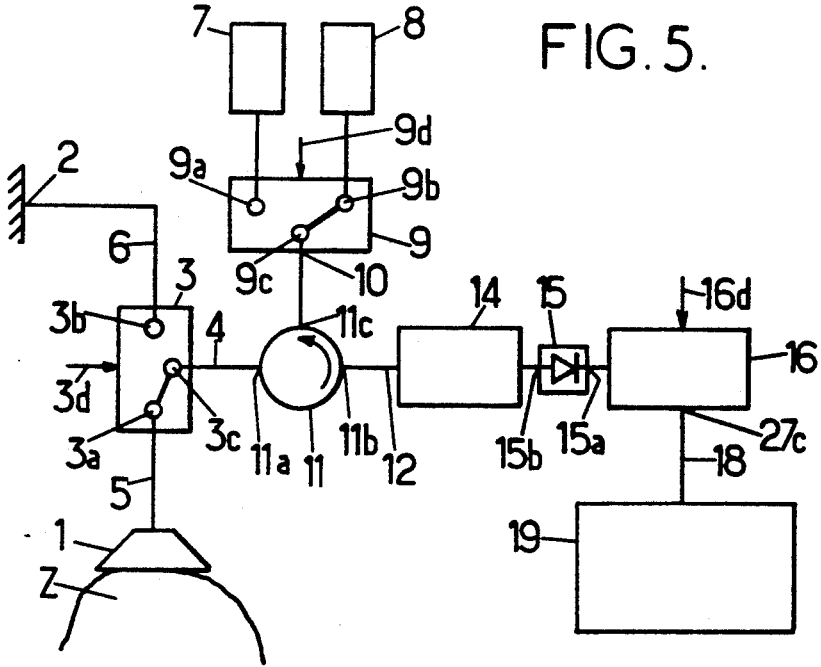

A synchronisation control circuit 17 acts, through its three control outputs 17a, 17b, 17c respectively on the input of the control 3d of the modulator 3, the control input 9d of the modulator 9 and the control input 16d of the two detectors by sampling the unit 16 to perform the sequencing of the two modulators 3 and 9 following the cycle of the four following phases, for output at 27c and transmission through the line 18:

| | |
|---|---|
| phase 1 | modulator 3 in position 3b |
| (FIG. 2) | modulator 9 in position 9a |
| phase 2 | modulator 3 in position 3a |
| (FIG. 3) | modulator 9 in position 9a |
| phase 3 | modulator 3 in position 3b |
| (FIG. 4) | modulator 9 in position 9b |
| phase 4 | modulator 3 in position 3a |
| (FIG. 5) | modulator 9 in position 9b |

Two particular embodiments of the sampling detector unit 16 and of the synchronisation control circuit 17 will be described below with reference to FIGS. 6 and 7.

It should be noted, that the thermal noise levels coming from the two temperature references 7 and 8, which are kept regulated at temperatures $T_1$ and $T_2$, being constant, the duration of connections, controlled by the synchronisation control circuits 17, on these references 7 and 8 and on the short circuit 2 (phases 1 and 3) may be very brief, of the order of 0.2 seconds for example, hence much briefer than the durations of connection of the references 7 and 8 on the detector 1, of the order of 2 seconds for example, namely a ratio of 1/10 for example between these two durations, whereas in prior devices with a single reference temperature the connection durations on the antenna and the short-circuit are equal.

Finally the line 18 is connected to the input of a micro-computer 19 (of which one embodiment will be described below with reference to FIG. 7) which determines the value of the absolute temperature T of the region Z as a function the reference temperatures $T_1$ and $T_2$, of the band width P of the device and of the coefficient of reflection r of the detector 1, as explained above, and marks the value of the temperature so calculated in a display device associated or incorporated (not illustrated).

In fact:
in phase 1 (FIG. 2), there is on the output 15a of the detector 15, calling K the Boltzman constant, a signal $S_1$ given by the formula $$S_1 = K \cdot P \cdot T_1$$

in phase 2 (FIG. 3), there is on the output 15a a signal $S_2$ given by the formula $$S_2 = K \cdot P[r \cdot T_1 + (1-r)T]$$

in phase 3 (FIG. 4), there is on the output 15a a signal $S_3$ given by the formula $$S_3 = K \cdot P \cdot T_2$$

in phase 4 (FIG. 5), there is on the output 15a a signal $S_4$ given by the formula $$S_4 = K \cdot P[rT_2 + (1-r)T]$$

Figure 6:
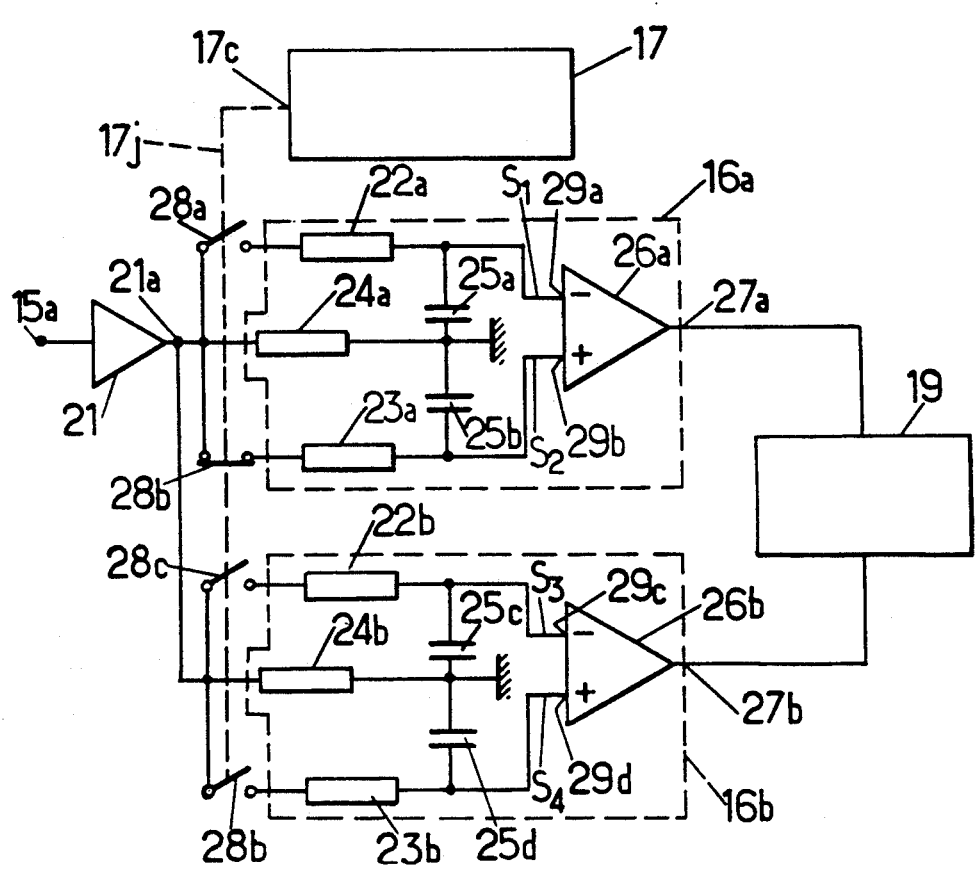

These four signals $S_1$, $S_2$, $S_3$, $S_4$ (which have thus been noted by simplification since, due to the fact of the activations of the tracks 1 and 2, by the first commutator and of the resistors $R_1$ referenced 7 and $R_2$ referenced 8, the complete notations should rather have been used $S_1R_1$, $S_2R_2$, $S_1R_2$ and $S_2R_2$ for respectively $S_1$, $S_2$, $S_3$, $S_4$), are processed in the detector by sampling 16 which can be performed as illustrated in FIG. 6, that is to say comprise:

a low-frequency amplifier 21, of gain equal at least to 5000, of which the input is connected to the output 15a of the microwave detector 15;

four switches 28a, 28b, 28c, 28d, of which one and one alone is closed, the three others being open, the successive closure of these four switches according to a cycle being actuated by the synchronisation control circuit 17 from its output 17c (control shown symbolically by the line 17j in interrupted lines) in correspondance with the four phases 1, 2, 3, 4 actuating the modulators 3 and 9 (FIG. 1), namely phase 1: 28a closed, the three other switches open
phase 2: 28b closed, the three other switches open
phase 3: 28c closed, the three other switches open
phase 4: 28d closed, the three other switches open
a set of two units 16a and 16b of the same structure.

The set of two units 16a and 16b comprise four averaging-integrators (with resistors 22a, 23a, 24a; 22b, 23b, 24b and capacitors 25a, 25b, 25c, 25d) corresponding to the four phases 1, 2, 3, 4 and hence to the four switches 28a, 28b, 28c, 28d and connected for the phases 1, 2, 3, 4, hence on the closure of the switch 28a, 28b, 28c, 28d, respectively and successively on the input 29a, 29b, 29c, 29d of two differential amplifiers 26a (of the unit 16a) and 26b (of the unit 16b).

The differential amplifier 26a effects the subtraction between the signal $S_1$ ("averaged" in the first averaging-integrator 22a, 25a) and the signal $S_2$ ("averaged" in the second averaging-integrator 23a, 25b) and delivers therefore a voltage Va, proportional to $S_a = S_1 - S_2$, available on the output 27a of the unit 16a, whilst the differential amplifier 26b performs the substractions between the signal $S_3$ ("averaged" in the third averaging-integrator 23b, 25d) and delivers therefore a voltage $V_b$, proportional to $S_b = S_3 - S_4$, available on the output 27b of the unit 16b.

The signals $S_1 - S_2$ and $S_3 - S_4$, available respectively at 27a and 27b, are then processed in the microcomputer 19.

Therefore there is obtained on the outputs 27a and 27b the following comparison of voltages of the phases 1 and 2 and of comparison of the phases 3 and 4:

Va proportional to $S_a = S_1 - S_2$ (phases 1 and 2)  (5)

Vb proportional to $S_b = S_3 - S_4$ (phases 3 and 4)  (6)

By replacing, in the formulae (5) and (6), $S_1$, $S_2$, $S_3$ and $S_4$ by their values given by the formulae (1), (2), (3) and (4) respectively, there results:

$$S_a = K \cdot P (1 - r)(T - T_1) \quad (7)$$
$$S_b = K \cdot P (1 - r)(T - T_2) \quad (8)$$

whence $$\frac{S_a}{S_b} = \frac{T - T_1}{T - T_2} \quad (9)$$

and hence $$\frac{V_a}{V_b} = \frac{T - T_1}{T - T_2} \quad (10)$$

whence finally $$T = \frac{V_a \cdot T_2 - V_b \cdot T_1}{V_a - V_b} \quad (11)$$

The value of the absolute temperature T of the region Z is hence calculable (in the microcomputer 19 of the FIG. 1) from $T_1$ and $T_2$ known and $V_a$ and $V_b$ voltages available in 27a for each cycle of four phases 1, 2, 3, 4, Va corresponding to the pair of phases 1-2 and $V_b$ to the pair of phases 3-4, without depending on the reflection coefficient r nor on the width P of the band width of the device.

On the contrary in a microwave radiometer of the prior art with a single temperature reference $T_R$ the single useful signal S (replacing the signals $S_a$ and $S_b$ of the device according to the invention) is given by the formula $S = K \cdot P (1 - r)(T - T_R)$ which depends on the coefficient of reflection r and on the width P of the band width, which necessitates a repeated calibration due to the fact that such a radiometer of the prior art can be derived thermally.

The value of T given by the formula (11) in the case of a device according to the invention is to be modified if it is desired to take into account losses of the modulator 9 and of the cables, denoted respectively by $p_1$ and $p_2$.

If the ambiant temperature is called $T_o$ in Kelvin degrees and if one puts $$T = T_o + dT$$
$$T_1 = T_o + dT_1$$
$$T_2 = T_o + dT_2$$

we have $$S_a = K \cdot P \cdot p_1 \cdot p_2 [dT_1 \cdot p_1 \cdot p_2 - dT](1-r) \quad (12)$$

$$S_b = K \cdot P \cdot p_1 \cdot p_2 [dT_2 \cdot p_1 \cdot p_2 - dT](1-r) \quad (13)$$

hence $$\frac{V_a}{V_b} = \frac{S_a}{S_b} = \frac{dT_1 \cdot p_1 \cdot p_2 - dT}{dT_2 \cdot p_1 \cdot p_2 - dT} \quad (14)$$

whence finally $$T = T_o + dT = T_o + \frac{V_b \cdot dT_1 \cdot p_1 \cdot p_2 - V_a \cdot dT_2 \cdot p_1 \cdot p_2}{V_a - V_b} \quad (15)$$

The values of $T_o$, $dT_1(=T_1-T_o)$ and $dT_2(=T_2-T_o)$ are known and $V_a$ and $V_b$ are determined as previously in a four-phase cycle; as for $p_1$ and $p_2$ they can be determined by replacing initially in the assembly of FIG. 1 (FIGS. 2,3,4 and 5) the detector 1 by a matched load of 50 ohms, for example, brought to a known temperature $T_c$ and by performing the cycle of the four phases 1,2,3,4 of FIGS. 2,3,4 and 5, which permits determination by the micro-computer 19 of the product $p_1 \cdot p_2$ by the formula (15) and memorising it in this micro-computer so that it then applies this formula 15 for the calculation of the temperature T of the zone Z when the detector 1 is placed in position (by replacing said matched resistor of 50 ohms) and effecting the cycle of the four phases.

Figure 7:
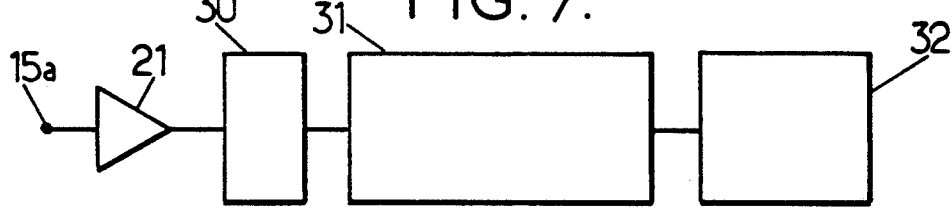
FIGS. 6 and 7 show, in diagramatic form, two particular embodiments of the detection of the four signals of the four phases of a cycle of operation of FIGS. 2 to 5 in a device according to FIG. 1.

The FIG. 7 illustrates another embodiment of a sampling detector 16.

According to the assembly of FIG. 7, the signal S emerging at 15a from the microwave detector 15 of FIG. 1 is applied to a low-frequency amplifier 21 (analogous to the amplifier 21 of FIG. 6) which is connected to an analog/digital converter 30.

A specimen is taken on the amplified signal and placed in digital form by means of the microcomputer 31 which processes this amplified and digitalised signal, whilst emitting synchronisation signals towards the modulators 3 and 9 (the micro-computer 31 playing the role of the micro-computer 19 and of the synchronisation circuit 17 of the embodiment of FIG. 1). The output from the microcomputer 31 is displayed in the display unit 32.

The sampling frequency is of the order of one kHz. A window, of about 2 seconds duration, enables the signals to be "averaged". This window is shifted on each new phase 1,2,3,4 of sampling.

FIG. 8 illustrates an embodiment (different from that of FIG. 1) of the two internal temperature references $T_1$ and $T_2$.

The unit 33, which comprises three resistor 34-transistor 35 fed a voltage source supply of +25 volts, associated with a differential amplifier 40, to a transistor 38 and to resistors 37a, 37b, 39, constitutes a regulated current generator adapted to attack a microwave avalanche diode 36, for example of the AILTECH NOISE GENE ROTOR 7618 type with a band pass of 1 to 18 GHz.

The differential amplifier 40 receives on its input (+) 40a, through the resistor 39 the voltage coming from the resistor 37b of value $r_b$ and on its input(−) 40b a voltage $E_1$ or $E_2$, according to the noise level to be generated. For example $E1 = 2$ volts and $E2 = 5$ volts.

To the voltage $E_1$ corresponds a current $I_1 = E_1/r_b$ and to the voltage $E_2$ a current $I_2 = E_2/r_b$.

The current flowing in the avalanche diode 36 has the same intensity as the current which flows in the resistor 37b.

The assembly of FIG. 8 supplies two current levels $I'_1$ (for the input voltage $E_1$) and $I'_2$ (for the input voltage $E_2$) to the avalanche diode 36 which will supply in response two equivalent reference noise levels at two reference temperatures $T_1$ and $T_2$.

Hence the input voltage $E_1$ of FIG. 8 corresponds to the resistance 7 of FIG. 1, whilst the input voltage $E_2$ of FIG. 8 corresponds to the resistance 8 of FIG. 1. The noise levels, corresponding to two temperatures $T_1$ and $T_2$, are available on the output 36a and applied, through a capacitor 36b, to an attenuator 13a and from there to the input 11c of the circulator 11 (FIG. 1).

This assembly of FIG. 8 with a two-voltage generator $E_1$ and $E_2$ and an avalanche diode is equivalent to two resistors (two noise sources) 7 and 8; the switch 9 of FIG. 1 is replaced by a modulation control (not illustrated) of the two levels $E_1$ and $E_2$.

The temperatures corresponding to the noise levels provided by the avalanche diode 36 being of the order of 1000° C., an attenuator (illustrated at 13 in FIG. 1) is used in order to bring these two temperature levels to those that are measured by the device according to the invention (for example 35° C. and 45° C. for $T_1$ and $T_2$ respectively.

Examples will now be given of the use of the radiometer according to the invention.

EXAMPLE 1

Measurement of a Temperature

Figure 9:
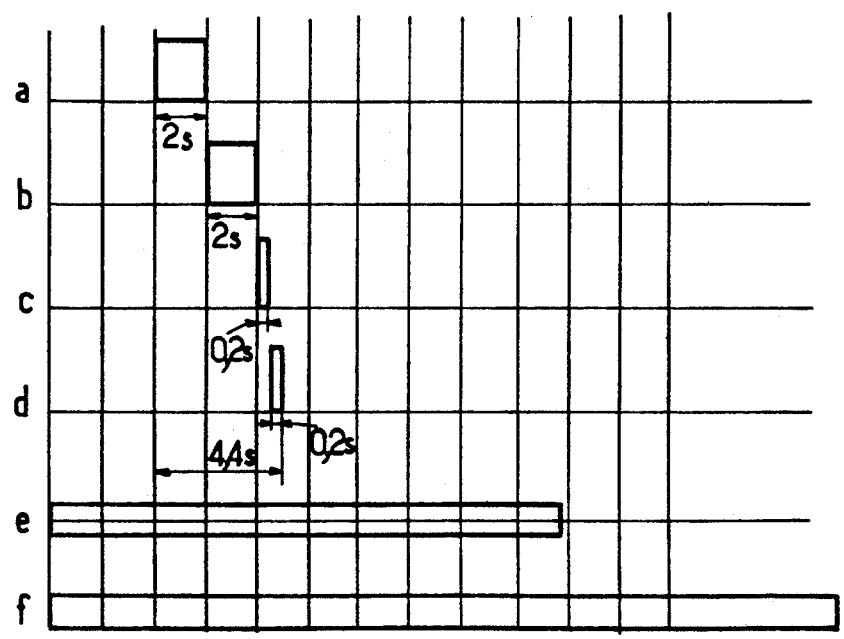
FIG. 9 is a time diagram of the operation of the device of FIG. 1 applied to the measurement of a temperature by means of a device according to the invention.

In FIG. 9 is shown, the time being plotted as abscissae, the acquisition periods, for the detector, the short-circuit and the two temperature reference sources, and the shifted windows for this detector and these sources.

Successively from top to bottom in this FIG. 9 there are shown:

- acquisition period a, of 2 seconds duration, of the detector 1 on the temperature reference 7 $T_1$ (phase 2),
- acquisition period b, of 2 seconds duration, of the detector 1 on the temperature reference 8 $T_2$ (phase 4),
- acquisition period c, of 0.2 second duration, of the short-circuit 2 on the temperature reference 7 $T_1$ (phase 1),
- the acquisition period d, of 0.2 second duration, of short-circuit 2 on the temperature reference 8 $T_2$ (phase 3),
- the shifted integration window e over 2 seconds for the detector, and
- the shifted integration window f over 20 seconds for the references.

As indicated above, the duration of measurement on the detector (2 seconds) may be greater than the measuring time of the short circuit for the temperature references (0.2 second), the thermal noise on these references being constant whence the possibility of distributing the sampling of this noise over a longer period.

With the above-mentioned values of 2 and 0.2 seconds, a measuring cycle of the temperature lasts 4.4 seconds (phases 1 to 4).

EXAMPLE 2

Microwave imagery with a detector Constituted by a Four Track Multi-Probe

Figure 10:
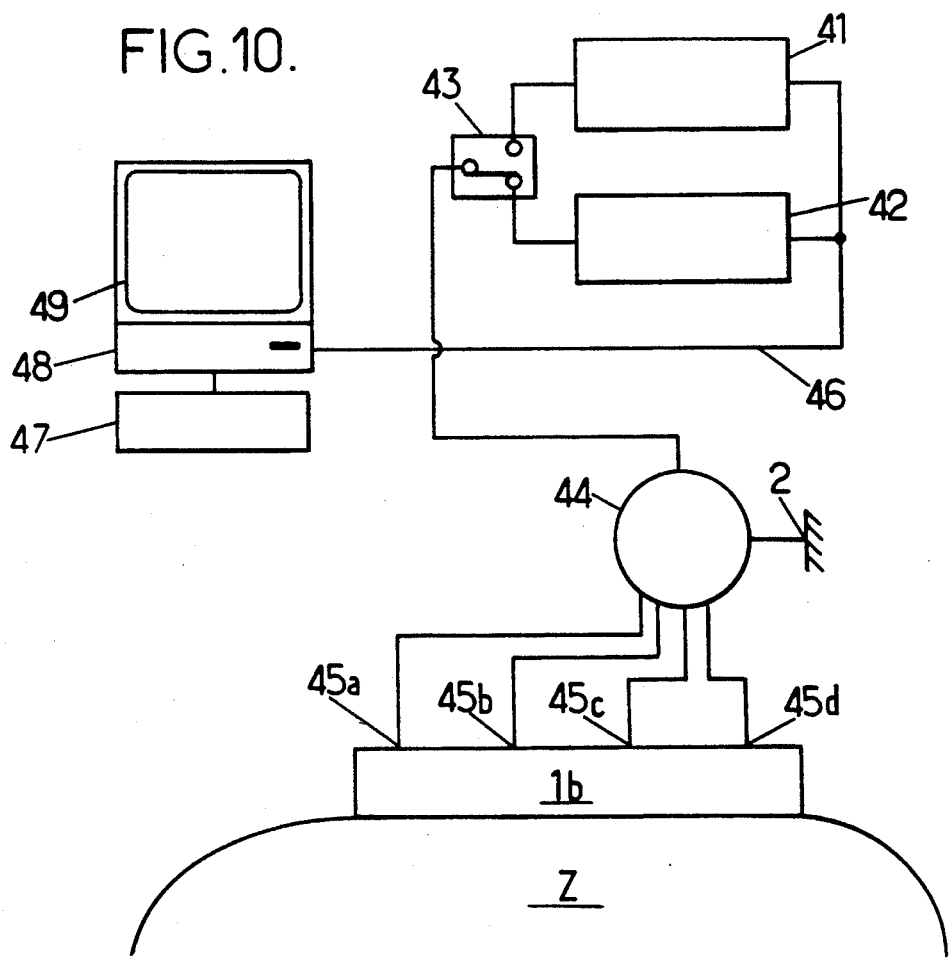
FIG. 10 illustrates, in the form of functional units, an imaging device with two radiometers according to the invention.

In FIG. 10, a unit comprising two radiometers 41 and 42 according to the invention is illustrated, of which the band passes are centered respectively on 3 GHz and 8.5 GHz, selectable by a microwave relay 43 with two tracks, supplied by a microwave multiplexer 44 with five tracks for the detector 1b to four tracks 45a, 45b, 45c, 45d, applied against the region Z, and a short-circuit 2.

The successive outputs of these four tracks, selected by the multiplexer 44, are applied by the relay 43 alternately at the radiometers 41 and 42 which on the single output line 46 are processed in a microcomputer 47 with a control unit 48 which controls also the radiometers 41 and 42, and a display device 49.

EXAMPLE 3

Automatic Control of the Temperature with Heating in Pulsed Mode

According to the prior art for hyperthermia with the temperature control by radiometry, two successive phases were provided for each hyperthermia session, namely a first heating phase which lasts about 60 seconds and the measurement phase which lasts about 9 seconds in the case of a radiometer centered on a frequency of 3 GHz, with a probe with two channels serving for the measurement of the temperature by radiometry.

As a consequence, the measurement of the temperature comprised three phases, the first phase being the measurement of the single reference of the temperature and the two other phases (second and third phases) serving to measure the two channels of the probe.

In such a hyperthermia system a punctual measurement was produced at the end of each heating cycle.

The temperature thus being defined, the computer determined the new value of the heating power to be injected, the control of the heating power being of proportional type, that is to say that the power was adapted to vary continuously between 0 watts and 50 watts for example.

With the device according to the invention with two reference temperatures, the power control may be effected by a modulation of the period of heating to maximum power. In this case the ratio between the duration of heating and the duration of radiometric measurement determines the average power injected for the heating, this duration of measurement being then used for the radiometric measurement. This is a novel feature of the operation of the device according to the invention.

The time of emission of maximum power depends therefore on the temperature measured at the moment concerned, on the one hand, and on the temperature that it is desired to reach in the region Z (for example 42° C. or 43° C.), on the other hand.

Such a method of practising the device according to the invention enables the development of the temperature to be checked more finely than with the prior art according to which the measurement was carried out at fixed periods. In the case of this novel method, a measurement at the end of each heating cycle on the one channel is effected and the average with the measurement of the preceding temperature is calculated.

EXAMPLE 4

Figure 11:
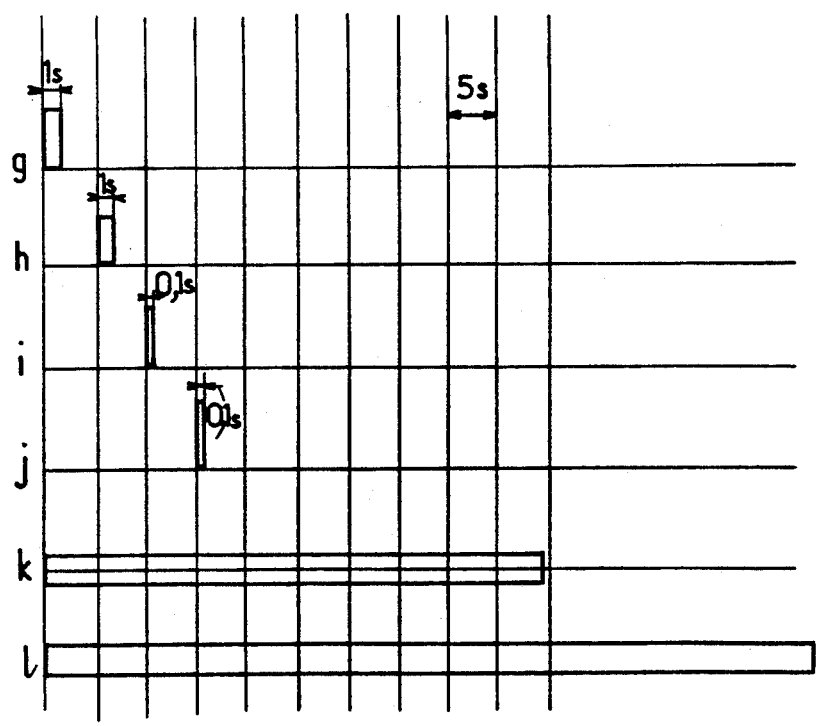
FIG. 11 is a time diagram of the operation, for a controlled hyperthermia system, of a device according to the invention.

Application of a Hyperthermia Device Controlled by Radiometry with a Two-Track Detector The cycle is illustrated in FIG. 11 in which times are plotted in abscissae and in which there is represented successively from top to bottom:

- the acquisition period g, of 1 second duration, of the detector on the temperature reference $T_1$
- the acquisition period h, of 1 second duration, of the detector on the temperature reference $T_2$,
- the acquisition period i, of 0.1 second duration, short circuit on the temperature reference $T_1$, the acquisition period j, of 0.1 second duration, the short circuit on the temperature reference $T_2$, the shifted integration window k, on 2 seconds for the detector, and the shifted integration window l on 20 seconds for the references.

This cycle is applied in particular within the framework of the novel method of modulation of the duration of heating (hyperthermia in pulsed mode).

EXAMPLE 5

Figure 12:
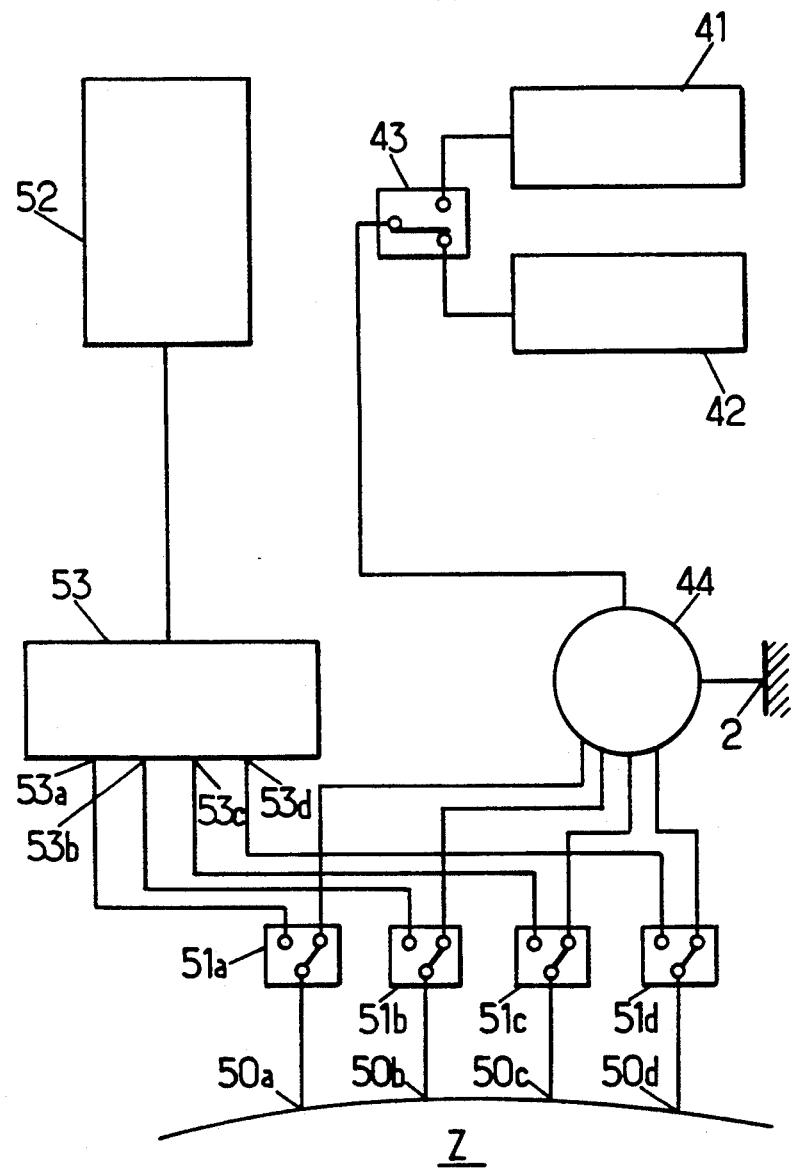
FIG. 12 illustrates an interstitiel hyperthermia device with two radiometers according to the invention.

Interstitial Hyperthermia Device Controlled by Two Radiometers, each with Two Temperature References In FIG. 12 is shown such a device employing first of all, as in example 10, two radiometers according to the invention, which the frequency band is centered effectively at 3 GHz and 8.5 GHz, with a microwave relay 43 with two channels selecting one or other of these two radiometers.

Equally as in the embodiment of FIG. 10, that of FIG. 12 comprises a microwave multiplexer 44 with five channels, of which one of these channels is constituted by the short circuit 2.

On the contrary the four other channels of the microwave multiplexer 44 are connected to four antenna detectors, of coaxial type, referenced 50a, 50b, 50c, 50d, implanted within of the zone Z to be heated and of which it is desired to measure the temperature, and this through four microwave switch relays 51a, 51b, 51c and 51d respectively.

The device of FIG. 12 comprises equally, on the one hand, a generator 52 to 915 MHz, of 50 watts power and a four-fold power divider, reference 53, which receives the output from the generator 52 and which supplies through its four outputs 53a, 53b, 53c, and 53d one of the two channels of each of the four microwave switch relays 51a, 51b, 51c, and 51d respectively.

The features of the operation of the device according to FIG. 12 are as follows:

maximum power: 50 watts
period for the modulation: 5 seconds
multi-track heating detector antenna, of which two are radiometric measurement channels
integration time: 2 seconds per channel and per temperature reference, namely four seconds in total for one channel
time necessary for one measurement: 8.4 seconds, namely two seconds per channel and per temperature reference and 0.1 second per temperature reference.

For different partial powers, the features are the following:

| 10 watts | modulation: | 1/5 |
| | duration of heating: | 1 second |
| | duration of measurement: | 4 seconds |
| | period: | 11 seconds |
| 20 watts | modulation: | 2/5 |
| | duration of heating: | 2 seconds |
| | duration of measurement: | 3 seconds |
| | period: | 15 seconds |
| 30 watts | modulation: | 3/5 |
| | duration of heating: | 3 seconds |
| | duration of measurement: | 2 seconds |
| | period: | 22.5 seconds |
| 40 watts | modulation: | 4/5 |
| | duration of heating: | 4 seconds |
| | duration of measurement: | 1 second |

-continued

| | |
|---|---|
| period: | 45 seconds |

In all cases the period of measurements is improved due to the arrangement according to the invention, which is particularly interesting whatever the hyperthermia system, in particular for interstitial hyperthermia systems and for hyperthermia systems of the prostate by endocavital applicators, since one obtains a follow-up practically in real time of the development of the temperature within the volume constituting the target (namely the tumor).

Finally in FIG. 13 is illustrated a particular embodiment of a wire antenna for an interstitial hyperthermia system.

Such an antenna is constituted by a coaxial cable 54, for example of the UT34 type, having an exterior diameter of 0.86 mm, of which a portion 54a of the length L has been bared, the length L depending on the frequency of the heating current and on the composition of the catheter 55 in plastic material which surrounds it. This catheter is for example of the type used in curietherapy to insert radioactive iridium wires into the heart of the tumor.

For a heating frequency of 915 MHz, the length L=39 mm is taken if the catheter is filled with water or 42 mm if the catheter is filled with air.

There is no relationship between these two lengths of 39 mm and 42 mm and a sub-multiple integer of the wave lengths in the medium. In fact in the heart of a tumor this wave length is 46.8 mm at the frequency of 915 MHz.

The adaptation coefficient is less than 0.05 at the heating frequency and about 0.1 in the band width of 3 to 4 GHz for a radiometer centered at 3.5 GHz and 8 to 9 GHz for a radiometer centered at 8.5 GHz.

As is self-evident, the invention is in no way limited to the types of application and the embodiments which ahve been more especially envisaged; it encompasses, on the contrary, all modifications.

We claim:

1. Method for the measurement of temperature of a region by using a micro-wave circuit comprising the steps of:

collecting through sampling during a first acquisition period, by means of a detector, the thermal noise microwaves emitted by said region, collecting by sampling during a second acquisition period, the thermal noise micro-waves generated from at least two internal temperature reference sources, generating, on the one hand, from said thermal noise microwaves emitted by said region and from a short circuit, and, on the other hand, from said thermal noise microwaves generated from each of said at least two reference sources, at least four resulting signals in order to determine a response indicating the temperature of said region in the absence of interfering influences produced by thermal derivatives or variations of the reflection coefficient of the detector with respect to said region.

2. Method according to claim 1, wherein an acquisition period of the detector on a reference source is greater by several times than an acquisition period of the short-circuit on a reference source.

3. Method according to claim 1, wherein shifted integration windows for the detector and for the references are employed.

4. Device for carrying out a method for the measurement of temperature of a region by collecting through sampling during an acquisition period, by means of a detector, the thermal noise microwaves emitted by said region and by using a microwave short circuit, said method further consisting in collecting by sampling during an acquisition period the thermal noise microwaves generated from at least two internal temperature reference sources so as to generate from said emitted or generated thermal noises microwaves at least four resulting signals in order to determine a response indicating the temperature of said region in the absence of interfering influences produced by thermal derivatives or variations of the reflection coefficient of the detector with respect to said region, wherein said device comprises:

- a microwave detector, a microwave short-circuit, a modulator, called below first modulator, with two connected input channels, one at the output of the detector and the other, at the microwave short-circuit and an output connectable to one or other of the two inputs, a circulator with three successive channels, the first one being connected to the output from the first modulator, the second one to the input of a microwave electronic processing unit and the third one constituting a reference input, said device comprising in addition at least two internal temperature reference sources and a second modulator with at least two input channels each connected to the output from said at least two references sources and an output connected to said third reference input of the circulator, possibly through an attenuator, said electronic processing unit comprising:
- a synchronisation control circuit acting both on the first modulator and on the second modulator to obtain at least four different successive output signals, each of said at least four signals corresponding to each of the at least four possibilities of connection of the two modulators, the first one to two input channels and the second one to at least two input channels;
- a microwave detector with one input connected, advantageously through a microwave amplifier, to the output of the circulator and one output; and
- a computer means connected to the output of said detector and adapted to process, under the control of said synchronisation control circuit, said at least four successive signals detected to deduce therefrom the temperature at the level of the detector, independently of the reflection coefficient of the detector with respect to the region and to the losses of the modulators and of the cables.

5. Device according to claim 4, wherein said computer means comprises a high-gain low-frequency amplifier, whose input is connected to the output of said microwave detector, at least four switches arranged in parallel between a common input connected to the output from said low-frequency amplifier and at least four output of at least one and one alone is supplied under the control of the synchronisation control circuit, in synchronisation with the control of the two modulators, to supply in its turn one, and one alone, among at least four averaging-integrators, and two differential amplifiers whose four inputs are connected each to the output of one of the four averaging-integrator to effect two differences, namely between output from the first averaging-integrator and the output of the second averaging-integrator, on the one hand, and between the output from the third averaging-integrator and the output of the fourth averaging-integrator, on the other hand.

6. Device according to claim 4, wherein said computer means comprises a high-gain, low-frequency amplifier whose input is connected to the output of said microwave detector, and an analog/digital converter of which the input is connected to the output of said low-frequency amplifier and of which the output is connected to the input of a processing unit.

7. Device according to claim 4, comprising, to obtain two different noise levels, a constant current generator, a differential amplifier which receives on one input the output from the regulated current generator, and on the other input one or other of two current values according to the voltage applied, an avalanche diode connected between the output of said differential amplifier and the output from the regulated current generator and a microwave attenuator receiving the output current from the avalanche diode to deliver on its output one or other of two signal corresponding to one or other of the two noise levels according to the value of the current applied to the other input of the differential amplifier.

8. Device according to claim 4, comprising a wire antenna constructed from a coaxial cable of which one portion is bared whose length which depends on the frequency of the heating current and the composition of the catheter which surrounds it, is not in relationship with the wavelength in the region.

9. Method of hyperthermia of a region and of measurement of the temperature thereof by microwave radiometry comprising the steps of:
- for the measurement of temperature of said region: (a) collecting through sampling during a first acquisition period, by means of a detector, the thermal noise microwaves emitted by said region and (b) by using a microwave short circuit, collecting by sampling during a second acquisition period the thermal noise microwaves generated from at least two internal temperature reference sources so as to generate from said emitted and generated thermal noises microwaves at least four resulting signals in order to determine a response indicating the temperature of said region in the absence of interfering influences produced by thermal derivatives or variations of the reflection coefficient of the detector with respect to said region,
- wherein said hyperthermia of said region is generated by controlling heating power, heating power control being effected by modulation of the period of heating to maximum power, the relationship between the heating period and the derivation of radiometric measurement determining the average power injected for the heating and this period of measurement serving for the radiometric measurement.

* * * * *